(12) United States Patent
Kuimelis

(10) Patent No.: US 6,436,665 B1
(45) Date of Patent: Aug. 20, 2002

(54) METHODS FOR ENCODING AND SORTING IN VITRO TRANSLATED PROTEINS

(75) Inventor: Robert G. Kuimelis, Brighton, MA (US)

(73) Assignee: Phylos, Inc, Lexington, MA (US)

( * ) Notice: Subject to any disclaimer, the term of this patent is extended or adjusted under 35 U.S.C. 154(b) by 36 days.

(21) Appl. No.: 09/648,040

(22) Filed: Aug. 25, 2000

Related U.S. Application Data

(60) Provisional application No. 60/151,261, filed on Aug. 27, 1999.

(51) Int. Cl.[7] .......................... C12P 21/06; C12P 19/34; C12Q 1/68; C07K 17/00; C07H 21/04
(52) U.S. Cl. .................. 435/68.1; 435/6; 435/69.1; 435/91.1; 530/350; 536/23.1; 536/24.2; 536/24.3
(58) Field of Search ............... 435/6, 68.1, 69.1, 435/91.1; 536/23.1, 24.2, 24.3; 530/350

(56) References Cited

U.S. PATENT DOCUMENTS

| | | | |
|---|---|---|---|
| 5,639,603 A | 6/1997 | Dower et al. | 435/6 |
| 5,863,722 A | 1/1999 | Brenner | 435/6 |
| 5,965,352 A | 10/1999 | Stoughton et al. | 435/4 |

FOREIGN PATENT DOCUMENTS

| | | |
|---|---|---|
| WO | WO 98/31700 | 7/1998 |
| WO | WO 99/51773 | 10/1999 |

OTHER PUBLICATIONS

Brenner and Lerner, "Encoded combinatorial chemistry," *Proc. Natl. Acad. Sci. USA* 89:5381–5383 (1992).

Cain et al., "Solution structure of a DNA hairpin and its disulfide cross–linked analog," *Nucleic Acids Res.* 23:2153–2160 (1995).

Gasparro et al., "Site–specific targeting of psoralen photo-adducts with a triple helix–forming oligonucleotide: characterization of psoralen monoadduct and crosslink formation," *Nucleic Acids Res.* 22:2845–2852 (1994).

Gryaznov and Letsinger, "Synthesis and properties of oligonucleotides containing aminodeoxythymidine units," *Nucleic Acids Res.* 20:3403–3409 (1992).

Krishnamurthy, "Pyranosyl–RNA: base pairing between homochiral oligonucleotide strands of opposite sense of chirality," *Agnew. Chem.* 35:1537–1541 (1996).

Nielsen et al., "Sequence–selective recognition of DNA by strand displacement with a thymine–substituted polyamide," *Science* 254:1497–1500 (1991).

Roberts and Szostak, "RNA–peptide fusions for the in vitro selection of peptides and proteins," *Proc. Natl. Acad. Sci. USA* 94:12297–12302 (1997).

*Primary Examiner*—David Guzo
*Assistant Examiner*—Katharine F Davis
(74) *Attorney, Agent, or Firm*—Clark & Elbing LLP

(57) ABSTRACT

Described herein are methods and reagents for encoding and sorting in vitro translated proteins.

45 Claims, 9 Drawing Sheets translation in microtiter tray --> fusion formation --> RNA degradation
Fig. 1A
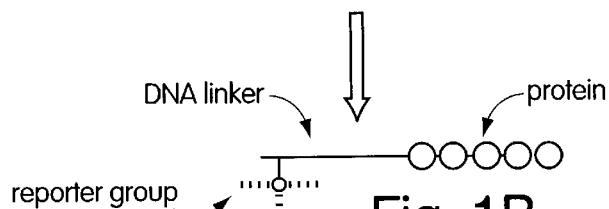
Fig. 1B
1) hybridize with encoding molecule:
2) trigger covalent cross-link
3) combine all "encoded" proteins
4) affinity isolation & concentration
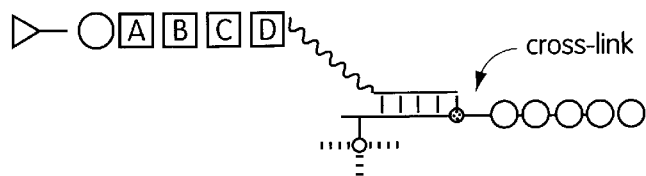
Fig. 1C
1) hybridize to universal chip or set of beads
2) trigger covalent cross-link
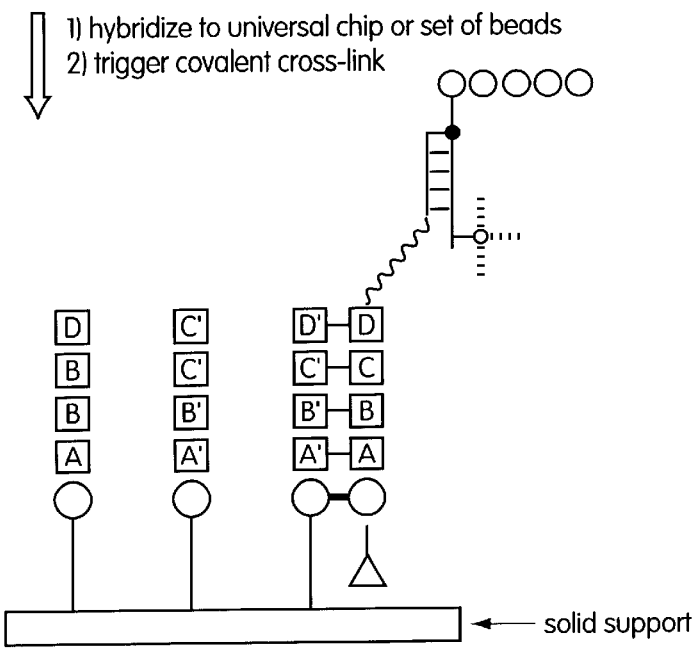
Fig. 1D B = biotin
S = 4-thio T
P = psoralen

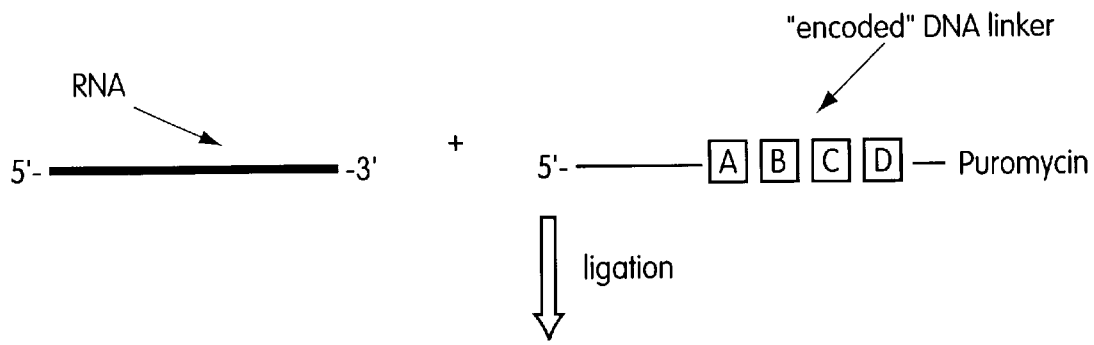
Fig. 4A
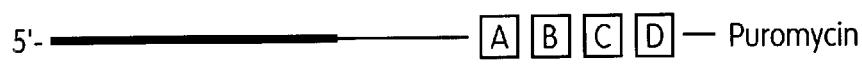
Fig. 4B
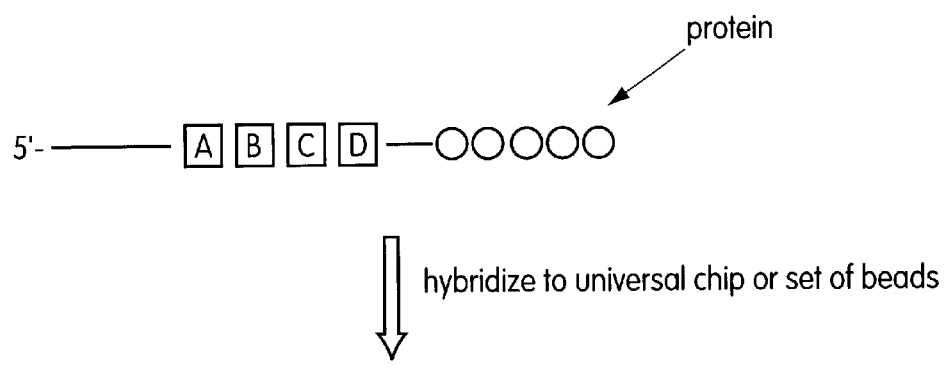
Fig. 4C
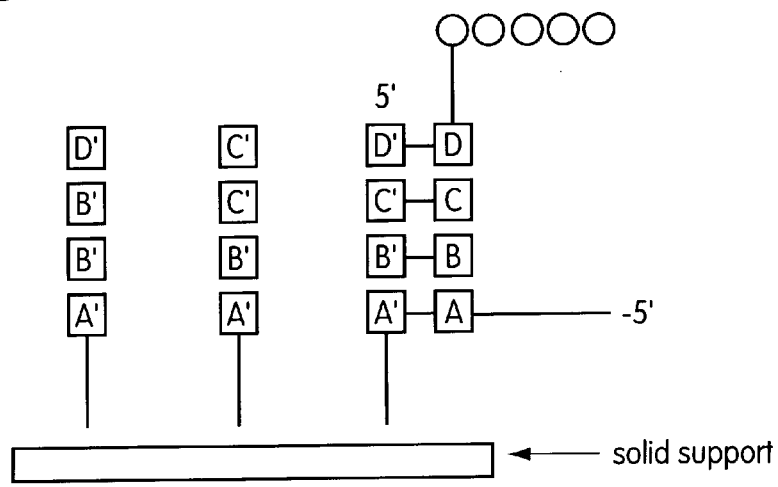

5'- AAA AAA AAA AAA |AACG||ACAA||AGGC||CAAC| CC — Puromycin

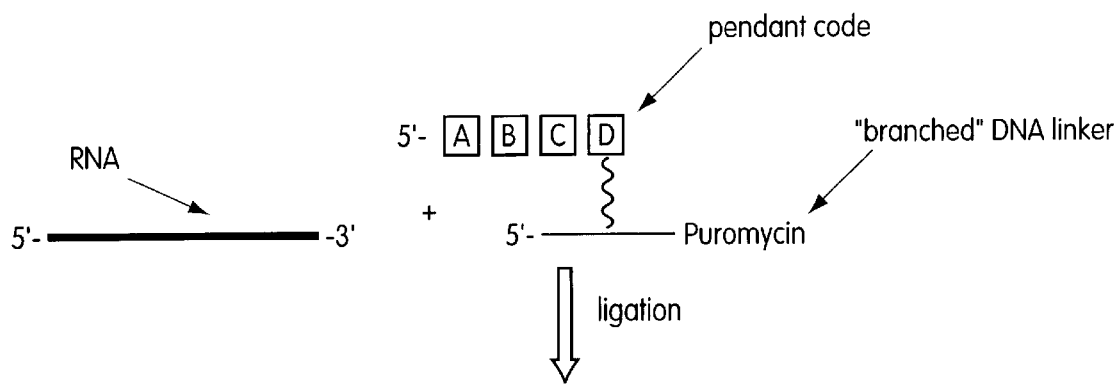
Fig. 8A
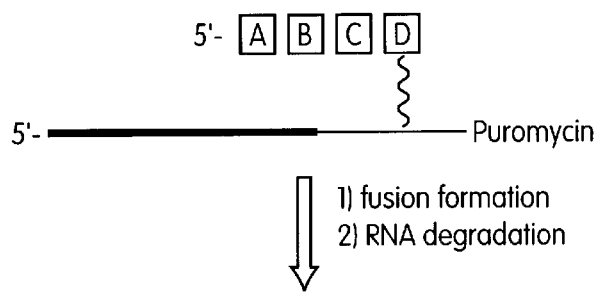
Fig. 8B
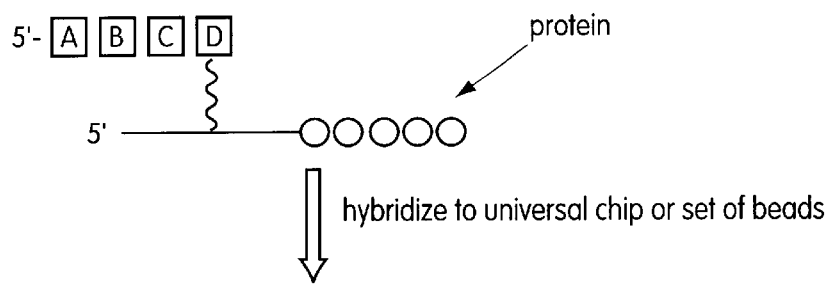
Fig. 8C
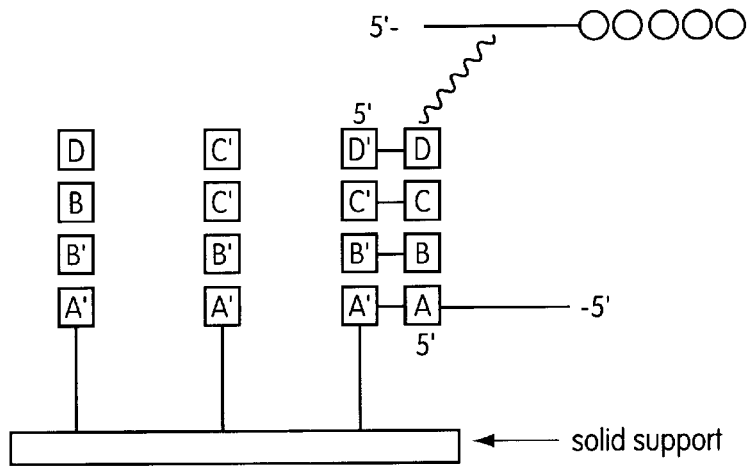

SEQUENCE LISTING

<160> NUMBER OF SEQ ID NOS: 11

<210> SEQ ID NO 1
<211> LENGTH: 31
<212> TYPE: DNA
<213> ORGANISM: Artificial Sequence
<220> FEATURE:
<223> OTHER INFORMATION: Addressing elements

<400> SEQUENCE: 1
aacgacaaag gccaactttt tttttttttt t                                   31

<210> SEQ ID NO 2
<211> LENGTH: 16
<212> TYPE: DNA
<213> ORGANISM: Artificial Sequence
<220> FEATURE:
<223> OTHER INFORMATION: Capture probe

<400> SEQUENCE: 2
ttgctgtttc cggttg                                                    16

<210> SEQ ID NO 3
<211> LENGTH: 30
<212> TYPE: DNA
<213> ORGANISM: Artificial Sequence
<220> FEATURE:
<223> OTHER INFORMATION: Addressing elements

<400> SEQUENCE: 3
aaaaaaaaaa aaaacgacaa aggccaaccc                                     30

<210> SEQ ID NO 4
<211> LENGTH: 30
<212> TYPE: DNA
<213> ORGANISM: Artificial Sequence
<220> FEATURE:
<223> OTHER INFORMATION: Encoding molecule
<221> NAME/KEY: misc_feature
<222> LOCATION: 10
<223> OTHER INFORMATION: n at position 10 can be a, t, c, or g.

<400> SEQUENCE: 4
aaaaaaaaan aaaaaaaaaa aaaaaaaacc                                     30

<210> SEQ ID NO 5
<211> LENGTH: 16
<212> TYPE: DNA
<213> ORGANISM: Artificial Sequence
<220> FEATURE:
<223> OTHER INFORMATION: Capture sequence

<400> SEQUENCE: 5
caagacactc atagcg                                                    16

<210> SEQ ID NO 6
<211> LENGTH: 16
<212> TYPE: DNA
<213> ORGANISM: Artificial Sequence
<220> FEATURE:
<223> OTHER INFORMATION: Capture sequence

<400> SEQUENCE: 6
caagacacac accaag                                                    16

```
<210> SEQ ID NO 7
<211> LENGTH: 16
<212> TYPE: DNA
<213> ORGANISM: Artificial Sequence
<220> FEATURE:
<223> OTHER INFORMATION: Capture sequence

<400> SEQUENCE: 7
caagacactc attcat                                                            16

<210> SEQ ID NO 8
<211> LENGTH: 16
<212> TYPE: DNA
<213> ORGANISM: Artificial Sequence
<220> FEATURE:
<223> OTHER INFORMATION: Capture Sequence

<400> SEQUENCE: 8
acaccaagag cgtcat                                                            16

<210> SEQ ID NO 9
<211> LENGTH: 29
<212> TYPE: DNA
<213> ORGANISM: Artificial Sequence
<220> FEATURE:
<223> OTHER INFORMATION: Encoding sequence

<400> SEQUENCE: 9
aaaaaaaaaa acttggtgtg tgtcttgcc                                              29

<210> SEQ ID NO 10
<211> LENGTH: 29
<212> TYPE: DNA
<213> ORGANISM: Artificial Sequence
<220> FEATURE:
<223> OTHER INFORMATION: Encoding sequence

<400> SEQUENCE: 10
aaaaaaaaaa aatgacgctc ttggtgtcc                                              29

<210> SEQ ID NO 11
<211> LENGTH: 20
<212> TYPE: DNA
<213> ORGANISM: Artificial Sequence
<220> FEATURE:
<223> OTHER INFORMATION: DNA splint
<221> NAME/KEY: misc_feature
<222> LOCATION: 11
<223> OTHER INFORMATION: n = A,T,C or G

<400> SEQUENCE: 11
tttttttttt nagcggatgc                                                        20
```

US 6,436,665 B1

METHODS FOR ENCODING AND SORTING IN VITRO TRANSLATED PROTEINS

This application claims the benefit of the filing date of U.S. provisional application, U.S. Ser. No. 60/151,261, filed Aug. 27, 1999.

BACKGROUND OF THE INVENTION

In general, the present invention relates to methods of generating fixed arrays of proteins or coded sets of protein-conjugated microparticles.

Certain macromolecules, such as proteins, are known to interact specifically with other molecules based on their three-dimensional shapes and electronic distributions. For example, proteins interact selectively with other proteins, nucleic acids, and small-molecules. The identification of molecules that interact with proteins lays the groundwork for the development of compounds to treat diseases and their associated symptoms.

The discovery of a single drug candidate can require the screening of thousands of compounds. It is therefore important to be able to screen large numbers of compounds rapidly and efficiently. One method for screening a large number of compounds is to fix candidate binding partners, such as proteins, to a solid support.

SUMMARY OF THE INVENTION

The present invention features methods for tagging or "encoding" individual in vitro translated proteins, or groups of in vitro translated proteins, with unique and minimal encoding molecules, and related methods for subsequently sorting those encoded molecules onto solid supports or microparticles. The present invention also features methods for the identification of a desired binding partner (for example, a protein or other compound) using the encoded and sorted proteins of the invention. The invention facilitates the isolation of proteins with desired properties from large pools of partially or completely random amino acid sequences. The invention also facilitates the use of automated approaches to protein or compound screening methods.

Accordingly, in a first aspect, the invention features a method for encoding and sorting an in vitro translated protein, involving the steps of providing an in vitro translated protein attached to a nucleic acid linker and attaching the protein, through the nucleic acid linker, to an encoding molecule, thereby encoding the protein.

In one embodiment, this method further involves immobilizing the encoded protein onto a solid support. In another embodiment, the candidate protein is derived from an RNA-protein fusion molecule. In yet another embodiment, the encoding molecule is made of nucleic acids, or nucleic acid analogs. Preferably, the encoding molecule comprises a unique addressing element, a linker-specific alignment element, and a linkage element between the addressing element and the linker-specific alignment element. Furthermore, the linkage element of the encoding molecule may include polyethylene glycol units (preferably, hexaethylene oxide). In yet another embodiment, the candidate protein is attached to the encoding molecule through hybridization of the linker-specific alignment element of the encoding molecule to the nucleic acid linker of the candidate protein, or to the protein itself.

In a second aspect, the invention features a method for encoding an in vitro translated protein, involving the steps of providing an in vitro translated protein and binding a nucleic acid linker to the protein, wherein the nucleic acid linker contains an addressing element, thereby encoding the protein.

In a preferred embodiment, this method further involves immobilizing he encoded protein onto a solid support. In another preferred embodiment, the candidate protein is derived from an RNA-protein fusion molecule.

In a third aspect, the invention features a method for encoding an in vitro translated protein, involving the steps of providing an in vitro translated protein and binding a nucleic acid linker to the protein, wherein an addressing element branches off from the nucleic acid linker, thereby encoding the protein.

In one embodiment, this method further involves immobilizing the encoded protein formed in the last step of the invention onto a solid support. In another embodiment, the candidate protein is derived from an RNA-protein fusion molecule. In yet another embodiment, the addressing element is bound to the nucleic acid linker by a linkage element. The linkage element of the encoding molecule may include polyethylene glycol units. Preferably, the polyethylene glycol units are hexaethylene oxide.

In yet other embodiments of each of the above aspects of the invention, the solid support is a glass or silica-based chip, or a bead. A capture probe may be attached to the solid support, and may consist of nucleic acids or nucleic acid analogs. The encoded candidate protein may be immobilized onto the solid support by hybridizing the encoded candidate protein to the nucleic acid capture probe, thus sorting the protein according to the information contained in the encoding molecule.

In further embodiments of all of the aspects of the invention, the candidate protein is labeled with a reporter tag, which is preferably a fluorophore. An affinity tag may also be attached to the encoding molecule. One exemplary affinity tag is biotin.

In yet further embodiments, the encoding molecule and solid support are functionalized with a cross-linking moiety. Preferably, the cross-linking moiety is a psoralen, azido compound, or sulfur-containing molecule. In one embodiment, he 5' terminus of the encoding molecule is functionalized with an electrophile that cross-links regioselectively with a nucleophilic amino acid side chain of the protein.

In a fourth aspect, the invention features a method for detecting an interaction between a protein and a compound, involving the steps of providing an encoded in vitro translated protein immobilized onto a solid support; contacting the protein with a candidate compound under conditions which allow an interaction between the protein and the compound; and analyzing the solid support for the presence of the compound as an indication of an interaction between the protein and the compound. The compound may be a nucleic acid, a protein, a therapeutic, or an enzyme.

In a fifth aspect, the invention features an in vitro translated protein attached to a nucleic acid linker and bound to an encoding molecule.

In a sixth aspect, the invention features an in vitro translated protein attached to an encoded nucleic acid linker molecule.

In a seventh aspect, the invention features an in vitro translated protein attached to a branched encoded nucleic acid linker molecule.

In various preferred embodiments, the protein is attached to a solid support bearing a capture probe. In other embodiments, the encoded protein is attached to the capture probe through hybridization or a covalent bond.

As used herein, by a "protein" is meant any two or more naturally occurring or modified amino acids joined by one or more peptide bonds. "Protein," "peptide," and "polypeptide" are used interchangeably.

By an "encoding molecule" is meant a unique tag which may be attached to a protein or peptide and which facilitates recognition of the protein among a population of proteins. The encoding molecule may be composed of nucleic acids, nucleic acid analogs, or non-nucleosides, but it is not comprised of the RNA that, when translated, yields the protein itself. By "encode" is meant to attach an encoding molecule.

By an "addressing element" is meant that portion of an encoding molecule which gives the encoding molecule its unique identity by differing sufficiently in sequence from other such elements in a given population. Preferably the addressing element is between 4 and 40 nucleotide units in length. In addition, the addressing element may comprise nucleic acids or nucleic acid analogs.

By a "linker-specific alignment element" is meant that portion of an encoding molecule which hybridizes to the nucleic acid linker of an in vitro translated protein, or to the protein itself. The addressing element may consist of nucleic acids or nucleic acid analogs.

By a "linkage element" is meant that portion of an encoding molecule that joins the addressing element and the linker-specific alignment element together. The linkage element may be composed of nucleic acids, nucleic acid analogs, and non-nucleosides. Preferably the linkage element includes polyethylene glycol units, and more preferably the polyethylene glycol units are hexaethylene oxide.

By "sort" is meant to position in an organized manner or otherwise identify or separate. Encoded proteins may be sorted onto a solid support.

By a "solid support" is meant any solid surface including, without limitation, any chip (for example, silica-based, glass, or gold chip), glass slide, membrane, bead, solid particle (for example, agarose, sepharose, polystyrene or magnetic bead), column (or column material), test tube, or microtiter dish.

By a "microarray" is meant a fixed pattern of immobilized objects on a solid surface or membrane. Typically, the array is made up of encoded proteins bound to capture probes which themselves are immobilized on the solid surface or membrane. "Microarray" and "chip" are used interchangeably. Preferably the microarray has a density of between 10 and 1000 objects/cm$^2$.

By "capture probe" is meant a sequence of deoxyribonucleotides, ribonucleotides, or analogs thereof, which hybridize in a sequence dependent manner to the addressing element of a unique encoding molecule in a population. The capture probe may consist of nucleic acids or nucleic acid analogs.

By "nucleic acid linker" is meant a sequence of deoxyribonucleotides, ribonucleotides, or analogs thereof. The nucleic acid linker is not comprised of the RNA that, when translated, yields the protein to which it is attached.

By an "encoded DNA linker" is meant a sequence of deoxyribonucleotides which contains an addressing element. In a "branched encoded DNA linker," the addressing element branches from an internal linker deoxyribonucleotide moiety. An encoded DNA linker may also comprise nucleic acid analogs.

By a "reporter tag" is meant a molecule whose presence can be monitored or detected. For example, the reporter tag can be a fluorophore.

By "therapeutic" is meant any molecule used to treat, ameliorate, improve, prevent, or stabilize a disease or symptom of a disease.

By an "RNA" is meant a sequence of two or more covalently bonded, naturally occurring or modified ribonucleotides. One example of a modified RNA included within this term is phosphorothioate RNA.

By "RNA-protein fusion" is meant an RNA molecule covalently bound to a protein.

By "functionalize" is meant to chemically modify in a manner that results in the attachment of a functional group or moiety. For example, an encoding molecule may be functionalized with an electrophile that cross-links regioselectively with a nucleophilic amino acid side chain of a protein or peptide. An encoding molecule or the capture probes of the solid support, in another example, can be functionalized with a cross-linking moiety such as psoralen, azido compounds, or sulfur-containing nucleosides.

The present invention provides a number of advantages. For example, the invention allows the employment of pre-made sets of universal encoding molecules, such as nucleic acids or nucleic acid analogues. These encoding molecules can be used in conjunction with corresponding universal microarrays or sets of microparticles to create novel protein-display systems. A system of pre-made encoding molecules is flexible, modular, scalable, and cost-effective. Another advantage of the present invention is the option of utilizing nucleic acid analogs which are not amenable to enzymatic incorporation or polymerization, but which are superior to conventional DNA or RNA in a number of respects. An additional advantage of the present invention is the ability to label proteins with fluorescent moieties, which can be used to monitor the protein in real time.

Yet another advantage of the present invention is the absence of RNA which encodes the protein in the final encoded and sorted product. This is important for several reasons. In particular, DNA is simpler to work with due to its chemical stability and its resistance to nucleases. In addition, the length of a protein's RNA is directly related to the protein's size, with large proteins possessing long RNA messages. Regions of these long RNAs sometimes have a propensity to adopt stable secondary structures which are difficult to predict, and these secondary structures can interfere with hybridization steps and protein folding and function. Accordingly, the development of a method to encode and sort proteins in the absence of the RNA which encodes the protein represents an advance in this field.

Other features and advantages of the invention will be apparent from the following detailed description, and from the claims.

DETAILED DESCRIPTION

The drawings will first briefly be described.

BRIEF DESCRIPTION OF THE DRAWINGS

FIG. 1A is a schematic representation of one exemplary step involved in the production of encoded and sorted in vitro translated proteins. In this step, an RNA molecule which is attached to a peptide acceptor through a DNA linker is in vitro translated to form an RNA-protein fusion molecule. The RNA portion of the fusion molecule is subsequently degraded by an RNase. The remaining portion of the fusion molecule contains a protein attached to a DNA linker.

FIG. 1B is a schematic representation of the protein portion of the fusion molecule remaining after degradation of the RNA as described in FIG. 1A.

FIG. 1C is a schematic representation of other exemplary steps involved in the production of encoded and sorted in vitro translated proteins. This step lists subsequent procedures involved in creating an encoded protein, including (i) hybridizing the DNA linker to a "unique encoding molecule," (ii) triggering a covalent cross-linking of the encoding molecule to the DNA linker, (iii) combining all encoded proteins into one solution, and (iv) isolating encoded proteins by affinity separation, followed by concentration of the protein products. The final product of these steps is a mixture of encoded in vitro translated protein.

FIG. 1D is a schematic representation of further exemplary steps involved in the production of encoded and sorted in vitro translated proteins. These further steps include (i) hybridizing the molecule formed in FIG. 1C, through the unique encoding molecule, to a universal chip or set of beads and (ii) triggering a covalent cross-link between the chip or bead and the unique encoding element. This step also illustrates the specific binding of an encoded protein to the capture probe of the solid support, and the lack of binding between an encoded protein and a capture probe which does not correspond to the encoded protein.

FIG. 4A is a schematic representation of one exemplary step involved in the production of encoded and sorted in vitro translated proteins using an encoded DNA linker. In this step an RNA molecule is ligated to an encoded DNA linker. The linker bears a code which will be used to bind the encoded protein to a solid support.

FIG. 4B is a schematic representation of other exemplary steps involved in the production of encoded and sorted in vitro translated proteins using an encoded DNA linker. These steps depict the translation of the RNA molecule which is attached to a peptide acceptor through an encoded DNA linker to form an RNA-protein fusion molecule, and subsequent degradation of the RNA portion of the fusion molecule by an RNase. The remaining portion of the fusion molecule contains a protein attached to an encoded DNA linker.

FIG. 4C is a schematic representation of a final exemplary step involved in the production of encoded and sorted in vitro translated proteins using an encoded DNA linker. This step shows the hybridization of the molecule formed in FIG. 4B, through the encoded DNA linker, to a universal chip or set of beads.

FIG. 8A is a schematic representation of one exemplary step involved in the production of encoded and sorted in vitro translated proteins using a branched encoded DNA linker. This step illustrates the ligation of an RNA molecule to a branched DNA linker.

FIG. 8B is a schematic representation of other exemplary steps involved in the production of encoded and sorted in vitro translated proteins using a branched encoded DNA linker. These steps comprise the translation of the RNA molecule which is attached to a peptide acceptor through a branched DNA linker to form an RNA-protein fusion molecule, and subsequent degradation of the RNA portion of the fusion molecule by an RNase. The remaining portion of the fusion molecule contains a protein attached to a branched DNA linker. The product of these steps is the protein portion of the fusion molecule remaining after degradation of the RNA.

FIG. 8C is a schematic representation of a final exemplary step involved in the production of encoded and sorted in vitro translated proteins using a branched encoded DNA linker. In this step the molecule formed in FIG. 8B is hybridized, through the addressing elements of the branched DNA linker, to a universal chip or set of beads.

Figure 2A:
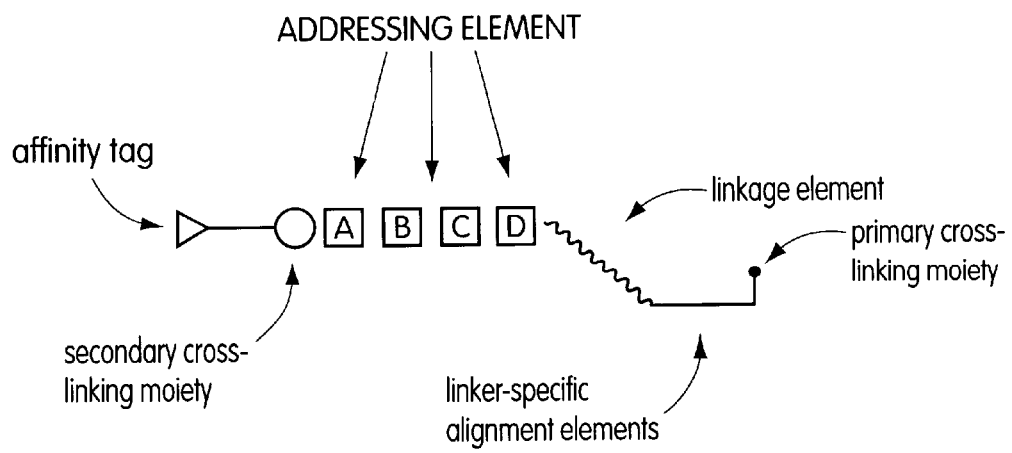
FIG. 2A is a schematic representation of an exemplary encoding molecule in general terms, which is used to encode a protein as described in FIGS. 1A–1D. The molecule comprises an addressing element attached to a linker-specific alignment element containing a primary cross-linking moiety, through a linkage element.

Described herein are methods of encoding and sorting in vitro translated proteins. Techniques for carrying out each method of the invention are now described in detail, using particular examples. These examples are provided for the purpose of illustrating the invention, and should not be construed as limiting.

EXAMPLE 1

Encoding and Sorting In Vitro Translated Proteins Using an Encoding Molecule

In vitro translated proteins can be encoded and sorted, for example, as shown in FIGS. 1A–1D. Individual RNA sequences (or a plurality of sequences) are translated in vitro, and RNA-protein fusions are formed, for example, according to the methods of Roberts and Szostak (Proc. Natl. Acad. Sci. USA 94:12297–12302, 1997) and Szostak et al. (WO 98/31700; U.S. Ser. No. 09/247,190), hereby incorporated by reference. The RNA for the in vitro translation reaction may be generated by any standard approach, including normal cellular synthesis, recombinant techniques, and chemical synthesis, and includes, without limitation, cellular RNA, mRNA libraries, and random synthetic RNA libraries. A peptide acceptor (for example, puromycin) is bonded to the RNA through a nucleic acid or nucleic acid analog linker. Exemplary nucleic acid analogs may be, for example, a PNA (Nielsen et al., Science 254:1497–1500, 1991), a P-RNA (Krishnamurthy, Agnew. Chem. 35:1537, 1996), or a 3'N phosphoramidate (Gryaznov and Letsinger, Nucleic Acids Res. 20:3403–3409, 1992). Such peptide acceptor molecules may be generated by any standard technique, for example, the techniques described in Roberts and Szostak (supra) and Szostak et al. (supra).

The RNA-protein fusion molecule preferably consists of an RNA molecule, which includes a translation initiation sequence and a start codon operably linked to a candidate protein coding sequence and a peptide acceptor at the 3' end of the candidate protein coding sequence. A DNA or RNase resistant nucleic acid analog sequence is included between the end of the message and the peptide acceptor. If desired, groups or collections of RNA sequences, for example, from a particular source or of a given type, may be translated together in a single reaction mixture according to the same general procedure.

If desired, the RNA protein fusion may be labeled with a reporter group, for example, a fluorescent reporter group. A fluorescent reporter group may be incorporated into the puromycin-containing DNA linker during the assembly of the DNA linker, for example, by modifying the general procedure as described by Roberts and Szostak (supra), replacing one or more of the nucleotides of the DNA linker with fluorescein dT (Glen Research, Sterling, Va.).

A suitable RNase devoid of DNase activity, for example, RNase I available from Ambion (Austin, Tex.), is then added to the fusion reaction to degrade the RNA portion of the RNA-protein fusion molecule.

Each remaining protein is then encoded as described below. For the encoding steps, individual proteins may be encoded, each with a unique encoding molecule. In this strategy, each encoded protein may be designed to correspond to only one capture probe during the sorting process, and the exact "address" of each protein on the solid support is therefore known. Alternatively, a plurality of proteins may be pooled and encoded with one or more encoding molecules. In this strategy, the same encoding element may encode one or more different proteins, and, when the encoded proteins are sorted, more than one encoded protein may bind to a specific capture probe. Therefore each "address" on the solid support may contain a mixture of proteins, each possessing the same encoding molecule.

Figure 2B:
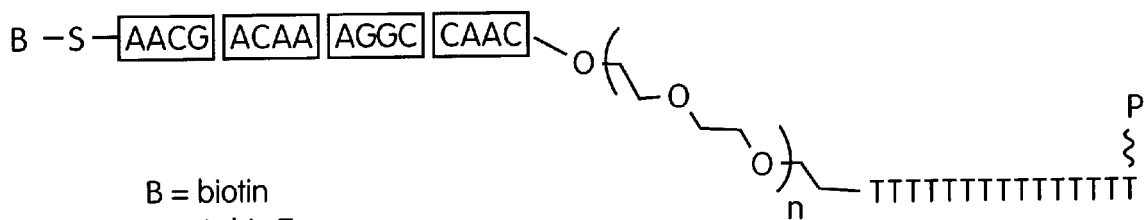
FIG. 2B is a schematic representation of an exemplary encoding molecule used to encode a protein as described in FIGS. 1A–1D, in which the affinity tag is biotin, the secondary cross-linking moiety is a sulfur-containing nucleoside, the boxed nucleotide sequences (SEQ ID NO: 1) represent the addressing elements, and the primary cross-linking moiety is psoralen. The addressing element is joined to the linker-specific alignment element through a hexaethylene oxide linkage element.

A unique encoding molecule, as shown, for example, in FIGS. 2A and 2B, in an approximately 1:1 molar ratio to the input RNA, is then added to each well. Each unique protein receives a different unique encoding molecule, and, since the identity of the unique encoding molecule is known, the identity of the protein may be determined. As shown in FIG. 2A, each unique encoding molecule includes three essential elements: a "linker-specific alignment element" which comprises nucleic acids or nucleic acid analogs and which binds either to the DNA linker positioned between the peptide acceptor and the in vitro translated protein or directly to the protein portion; an "addressing element" which comprises nucleic acids or nucleic acid analogs and which binds to a specific position on the solid support or to a specific microparticle; and a "linkage element" which connects the linker-specific alignment element and unique encoding element.

Simple unique encoding molecules can be assembled in the 3'→5' direction by conventional automated, solid-supported phosphoramidite oligonucleotide chemistry, for example, as described by Beaucage and Caruthers (Tetrahedron Letters 22:1859, 1981). For example, the synthesis of the exemplary encoding molecule shown in FIG. 2B begins with a solid support (e.g., controlled-pore glass or polystyrene) functionalized with an A monomer at the nucleoside's 3'-hydroxyl group. Additional monomers are coupled stepwise until the desired encoding sequence has been built up. Design rules for specific encoding sequences are described in U.S. Pat. No. 5,863,722. After the encoding sequence has been assembled, four hexaethylene oxide monomer units (Glen Research) are added to provide the flexible linkage element. The linker-specific alignment element is added next. In the event that the fusions are prepared with the standard 30P DNA linker, as described by Roberts and Szostak (supra), a 15-mer poly-T alignment element is added. If other DNA linkers are utilized in the preparation of the fusions (i.e., not 30P), then the alignment element must be the reverse-complement of some region of the DNA linker sequence. Finally, if desired, a psoralen phosphoramidite (Glen Research), or an equivalent phosphoramidite moiety, is added at the 5'-terminus to function as the primary crosslinking moiety.

Upon completion of synthesis, the encoding molecule is cleaved from the support and deprotected with ammonium hydroxide using methods known to those skilled in the art. Final purification is accomplished by standard chromatographic or electrophoretic techniques.

The simple unique encoding molecules can be readily elaborated to give an expanded encoding molecule. For example, as described above, the unique encoding molecule, typically at the linker-specific alignment element, may be functionalized with a primary cross-linking moiety, for example, psoralen, which is used to permanently crosslink the unique encoding species to the in vitro translated protein. The addressing element may also be functionalized, with a secondary cross-linking moiety, for example, 4-thio T, to form a covalent bond between the solid support and the unique encoding molecule. Moreover, the addressing element may be further labeled with an affinity tag, for example, biotin, which may be used in the isolation and concentration of the encoded proteins. The affinity tag is incorporated as a 3'-support (Glen Research) and the rest of the encoding molecule is constructed as described above. In one particular embodiment, the linkage element of the unique encoding molecule consists of polyethylene glycol units, for example, hexaethylene oxide.

The unique encoding molecules are hybridized to the proteins through an interaction between the linker-specific alignment element of the encoding molecule and the DNA linker of the protein fusion using standard hybridization conditions known to those skilled in the art, as shown, for example, in FIG. 1C. The unique encoding molecule is then covalently cross-linked to either the DNA linker of the protein or to the protein itself, using ultraviolet light, typically at 350 nm. If the encoding molecule is to be covalently cross-linked to the DNA linker of the protein, a crosslinking agent such as psoralen may be used, for example according to the methods of Gasparro et al. (Nucleic Acids Research, 22:2845–2852, 1994). Alternatively, if the encoding molecule is to be covalently crosslinked to the protein directly, then a cross-linking agent such as an azido compound may be used, for example, according to the methods of Bayley (Photogenerated Reagents in Biochemistry and Molecular Biology, Elsevier, N.Y., 1983).

The solutions containing proteins cross-linked to unique encoding molecules are then combined and isolated by standard affinity separation, for example, by applying the biotinylated proteins to a streptavidin column using standard techniques. Other standard affinity separation techniques may be used according to the affinity tag which is attached to the encoding molecule.

Figures 3A, 3B:
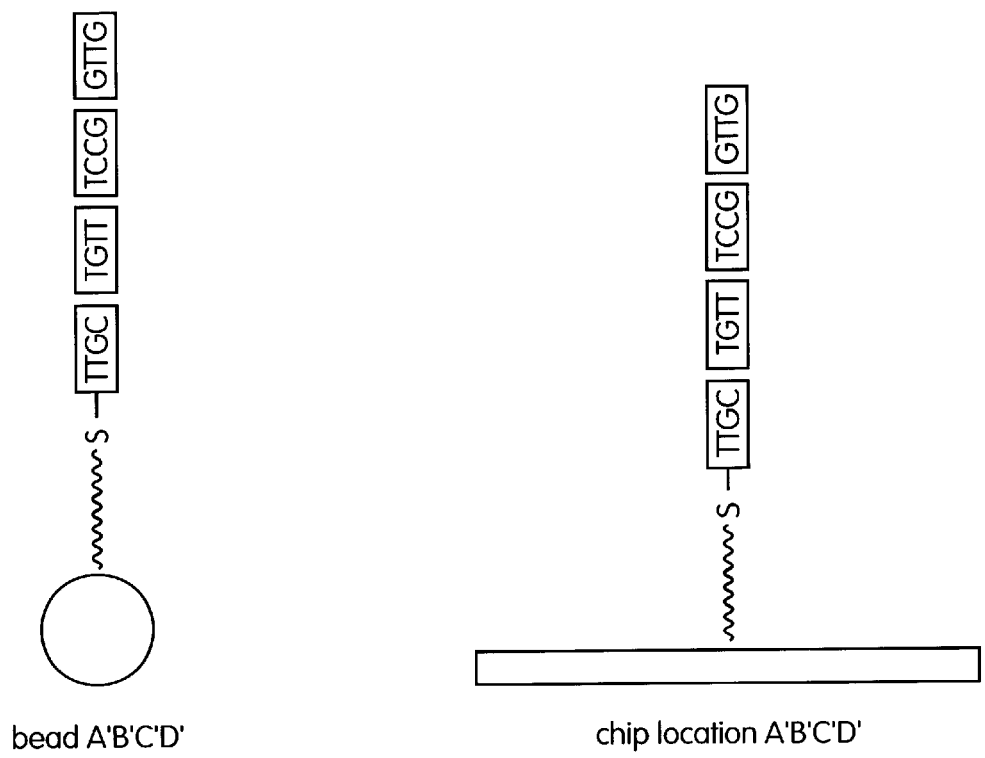
FIG. 3A is a schematic representation of an example of a solid support, a bead, which may be used in the present invention to create protein-display systems. The sequence (SEQ ID NO: 2) of the capture probe is designed to bind the encoding molecule of example 2B.
FIG. 3B is a schematic representation of an example of a solid support, a chip, which may be used in the present invention to create protein-display systems. The sequence (SEQ ID NO: 2) of the capture probe at the indicated location of the chip is designed to bind the encoding molecule of example 2B.

The affinity-separated solution containing the encoded proteins is then applied to a solid support, as shown, for example, in FIG. 1D. Preferably, the solid support is a universal chip or a universal set of coded microparticles, for example as described by Fulton et al. (Clinical Chemistry 43:1749–1756, 1997) and, as shown in FIGS. 3A and 3B, containing capture probes designed to interact with the encoded proteins. The capture probes are preferably nucleic acids or nucleic acid analogs which bind to the unique encoding element of the encoding molecule in a sequence specific manner, thereby linking the protein to the solid support and sorting the protein. Each capture probe on the solid support is designed to comprise a different nucleotide sequence, each of which binds a different encoding molecule-protein complex. The capture probe may also contain a molecule, for example, 4-thio T, which upon oxidation can be used to crosslink the capture probe to the encoding molecule via the secondary crosslinking moiety (as described above).

The capture probes may be attached to the solid support by any method, for example, those methods described in Kuimelis et al. (U.S. Ser. No. 09/282,734, filed Mar. 31, 1999, and WO 99/51773, published Oct. 14, 1999). In one exemplary method for attaching the capture probes to the solid support, the capture probes are adjusted to a concentration of 500 $\mu$M in 100 mM sodium carbonate buffer (pH 9.0), and are applied to the derivatized surface of the solid support at defined positions. A three axis motion control apparatus coupled to a microvolume liquid delivery system may be used to accurately deposit the capture probes. The solid support containing the deposited capture probes is incubated at room temperature in a moisture-saturated environment for at least two hours. The attachment reaction is terminated by immersing the glass surface in an aqueous 1% ammonia solution for five minutes with gentle agitation. The glass surface is then subjected to three 5-minute washes, using fresh portions of distilled water for each wash. The array is then soaked in 1 M phosphate buffered saline (PBS) solution for 2 hours at room temperature, then rinsed again for 5 minutes in distilled water.

The "sorted" proteins can be covalently linked to the capture probes, for example, by triggering disulfide bond formation at the terminus of the duplex according to the methods of Cain et al. (Nucleic Acids Research, 23:2153–2160, 1995).

EXAMPLE 2

Encoding and Sorting In Vitro Translated Proteins Using an Encoded DNA Linker

To further simplify the encoding process, in vitro translated proteins may also be generated from RNA molecules joined directly to unique encoding molecules in the form of encoded DNA linkers, as shown in FIGS. 4A–4C. The encoded DNA linker may consist of nucleic acids or nucleic acid analogs, and an "addressing element" which comprises nucleic acids or nucleic acid analogs that bind to a specific position on the solid support or to a specific microparticle.

Simple encoded DNA linker molecules can be assembled in the 3'→5' direction by conventional automated, solid-support phosphoramidite oligonucleotide chemistry for example, as described by Beaucage and Caruthers (supra). For example, the synthesis of the exemplary encoded DNA linker molecule shown in FIG. 5B begins with a solid support (e.g., controlled-pore glass or polystyrene) functionalized with a peptide acceptor, for example, puromycin at the nucleoside's 2'-hydroxyl group (Glen Research). Two C monomers are then added. Next, the desired encoding sequence is built up by the stepwise addition of appropriate monomers. Design rules for specific encoding sequences are disclosed in U.S. Pat. No. 5,863,722. Twelve A monomers are coupled stepwise to finish the construction of the DNA linker. The overall length of the encoded DNA linker molecule is preferably the same as the 30P DNA linker employed by Roberts & Szostak (supra). Upon completion of synthesis, the encoding molecule is cleaved from the support and deprotected in the usual fashion with ammonium hydroxide. Final purification is accomplished by standard chromatographic or electrophoretic techniques.

Figures 5A, 5B:
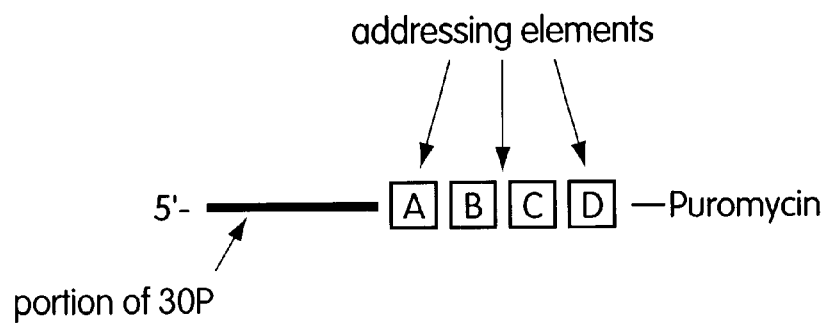
FIG. 5A is a schematic representation of an exemplary encoding molecule used to encode a protein as described in FIGS. 4A–4C, in general terms, comprising a DNA linker containing addressing elements and a peptide acceptor, for example, puromycin.
FIG. 5B is a schematic representation of an example of an encoding molecule (SEQ ID NO: 3) used in the invention used to encode a protein as described in FIGS. 4A–4C, wherein the boxed nucleotide sequences represent the addressing elements.

If desired, the simple encoded DNA linker molecules can be readily elaborated with an affinity tag (e.g., biotin) and/or a fluorophore (e.g., fluorescein) to give an expanded encoded DNA linker molecule. The affinity tag and fluorophore are each incorporated as nucleobase-functionalized T monomers (Glen Research) in the poly A region of the encoding molecule, replacing one/two of the twelve A monomers as shown in FIG. 5B. The remainder of the encoding molecule is constructed as described already for the simple encoded DNA linker.

The encoded DNA linker, which is phosphorylated at its 5' end, is ligated to the RNA using, for example T4 DNA ligase, as shown in FIG. 4A. The ligated product is then in vitro translated according to the methods of Roberts and Szostak (supra) and Szostak et al. (supra), to form an RNA-protein fusion molecule, and the RNA portion of the molecule is then degraded as described in Example 1, and as shown in FIG. 4B. This RNA degradation step results in an in vitro translated protein attached to an encoded DNA linker.

The encoded in vitro translated protein may be hybridized to a universal chip or set of beads as shown in FIG. 4C. Hybridization occurs between the addressing element of the DNA linker and the capture probe of the solid support as described in Example 1.

Using the techniques essentially as described above, a polypeptide that binds TNF-α and a polypeptide that binds IL-13, were in vitro translated, encoded, sorted, and shown to bind TNF-α, and IL-13, as follows.

Unique sequences, based on four consecutive 4-nucleotide blocks, were selected to serve as capture points to both sort and anchor the encoded polypeptides. The following is a list of the capture (sorting) sequences that were employed (written 5'→3'):

TAG_CP-4=CAAGACACTCATAGCG-(HEO)$_4$—NH$_2$ (SEQ ID NO: 5)

TAG_CP-8=CAAGACACACACCAAG-(HEO)$_4$—NH$_2$ (SEQ ID NO: 6)

TAG_CP-12=CAAGACACTCATTCAT-(HEO)$_4$—NH$_2$ (SEQ ID NO: 7)

TAG_CP-16=ACACCAAGAGCGTCAT-(HEO)$_4$—NH$_2$ (SEQ ID NO: 8)

The oligonucleotides were prepared with an automated DNA synthesizer (PE BioSystems Expedite 8909) using conventional phosphoramidite chemistry, and reagents from Glen Research. Synthesis was initiated with a solid support bearing an orthogonally protected amino functionality, whereby the 3'-terminal amine is not unmasked until the final deprotection step. The first four monomers to be added were hexaethylene oxide units (HEO), followed by the standard A, G, C, and T monomers. Oligonucleotides were cleaved from the solid support and deprotected with ammonium hydroxide, concentrated to dryness, precipitated in ethanol, and purified by reverse-phase HPLC using an acetonitrile gradient in triethylammonium acetate buffer. Appropriate fractions from the HPLC were collected, evaporated to dryness in a vacuum centrifuge, and then co-evaporated with a portion of water.

The purified, amine-labeled oligonucleotides were adjusted to a concentration of 500 μM in 50 mM sodium carbonate buffer (pH 9.0). These sorting sequences were spotted onto the amine-reactive glass surface (3D-Link, Surmodics) at defined positions in a 5×5×4 array pattern with a 3-axis robot (MicroGrid, BioRobotics). A 4-pin tool was used to transfer the liquid from a 384-well microtiter plate, producing 200 micron features with a 600 micron pitch. Each sub-grid of 24 features represents a single oligonucleotide (i.e., 24 replicate spots). The printed arrays were incubated at room temperature in a moisture-saturated environment for 12–18 hours. The attachment reaction was terminated by immersing the chips in 2% aqueous ammonium hydroxide for five minutes with gentle agitation, followed by rinsing with distilled water (3×5 minutes).

Unique encoded DNA linkers were then synthesized with a 5'-terminal dA11 tract, followed by unique 16-mers comprised of 4-nucleotide blocks, dC2 and finally a puromycin at the 3' terminus, similar to the encoding molecule of FIG. 5B. The encoding sequences were as follows, and were designed to work in conjunction with the capture probe sequences described above (written 5'→3'):

TAG_LN-8= AAAAAAAAAAACTTGGTGTGTGTCTTGCC-puromycin (SEQ ID NO: 9)

TAG_LN-16= AAAAAAAAAAAATGACGCTCTTGGTGTCC-puromycin (SEQ ID NO: 10)

The encoded DNA linkers were prepared with an automated DNA synthesizer essentially as described above, using conventional phosphoramidite chemistry. All reagents were from Glen Research. Synthesis was initiated with a solid support bearing a protected puromycin moiety. Oligonucleotides were cleaved from the solid support and deprotected with ammonium hydroxide, concentrated to dryness, and then precipitated in ethanol. Purity and integrity were confirmed by anion-exchange HPLC.

Common PCR primers were used to amplify regions of DNA that encode polypeptide sequences that bound TNF-α and IL-13, denoted as FnTNF and FnIL13, respectively. The 3'-primer contained an additional AGCGGATGC sequence at the end. Standard PCR amplifications were carried out using the primers and templates in the presence of PCR reagents (Ready-to-go beads, Amersham) for 25 cycles. The integrity of the PCR products was confirmed on a 2% agarose gel. The FnTNF and FnIL13 sequences were then in vitro transcribed (Mega Short Script, Ambion) from the PCR products according to standard protocols and purified on a NAP-25 size-exclusion column (Amersham Pharmacia). The resulting RNA-containing fractions were precipitated and resuspended in H$_2$O.

The FnTNF and FnIL13 RNA constructs were enzymatically ligated to 5' phosphorylated unique encoding sequences. FnTNF RNA was ligated to TAG_LN-8, and FnIL13 was ligated to TAG_LN-16, yielding the following RNA-DNA linker-puromycin chimeras: FnTNF_LN-8 and FnIL13_LN-16, respectively. Ligation was performed on a 1 nanomole scale with equimolar amounts of RNA and 5' phosphorylated encoding DNA-puromycin linker, utilizing 100 units T4 DNA ligase (Promega) in the presence of 1 nanomole of a common DNA splint, TTTTTTTTTT-NAGCGGATGC (SEQ ID NO: 11). The incubations were carried out at 16° C. for 12–18 hours, and the ligation products were separated by denaturing PAGE (6% TBE-Urea). The ligated products were visualized by UV shadowing, excised, eluted from the gel by crushing and soaking, and subsequently precipitated and resuspended in H$_2$O.

In vitro translation of the purified ligation products was carried out according to the following procedure: 83 μL ligated RNA (120 pmol) in H$_2$O was added to 15 μL master mix (Ambion, without methionine), 2 μL $^{35}$S-met (15 μM) and 200 μL of rabbit reticulocyte lysate (Ambion) for a total volume of 300 μL. The reaction mixture was incubated for 30 minutes at 30° C., and then 100 μL 2 M KCl and 20 μL 1 M MgCl$_2$ was added. After a further 60 minutes incubation at room temperature, 47 μL 0.5 M EDTA was added.

The resulting encoded RNA-linker-protein fusions, FNTNF_LN-8 and FNIL13_LN-16, were subsequently isolated by oligo-dT chromatography. An equal volume of 2× oligo dT binding buffer (200 mM Tris; pH 8, 2 M NaCl, 20 mM EDTA, and 0.1% Tween-20) was added to the reactions, and the RNA-linker-fusions were then bound to 100 mg oligo dT cellulose (Pharmacia), rinsed with wash buffer (100 mM Tris pH 8, 1 M NaCl, 0.05% Tween-20), and eluted with H$_2$O. Quantitation of the RNA-DNA linker fusions was done by scintillation counting, and the integrity of the fusions was confirmed by PAGE (4–20% Tris-glycine).

The FNTNF_LN-8 DNA-protein fusions were then sorted on a microarray. Fifty fmol of fusion was adjusted to 5× SSC containing 0.05% Tween-20 in a total volume of 350 μL. The RNA was then digested by adding 2 μL RNase A (Ambion) at 37° C. for 15 minutes, leaving just the 29-mer DNA containing the 16-nucleotide encoding sequence, in this case TAG_LN-8, fused to the protein. The entire volume was applied to the microarray under a 400 μL gasket device, and the assembly was continuously rotated for 18 hours at room temperature. After sorting, the slide was washed sequentially with stirred 500 mL portions of 2.5× SSC, 1×SSC, and 0.5×SSC for 5 minutes each at room temperature. Traces of liquid were removed by centrifugation and the slide was allowed to air-dry.

The sorted polypeptide was visualized by direct detection of the $^{35}$S methionine on the fusion protein by phosphorimage analysis with a Molecular Dynamics Storm system. Exposure time was 48 hours with direct contact between the microarray and the phosphor storage screen. Phosphorimage scanning was performed at the 50 μm resolution setting and data was extracted with ImageQuant v.4.3 software.

The functionality of the sorted polypeptide was demonstrated by binding to labeled TNF-α protein. Recombinant human TNF-α (500 μg, PeproTech) was taken up in 230 μL 1×PBS and dialyzed against 700 mL stirred 1×PBS at 4° C. for 18 hours in a Microdialyzer unit (3,500 MWCO, Pierce). The dialyzed TNF-α was treated with EZ-Link NHS-LC-LC biotinylation reagent (20 μg, Pierce) for 2 hours at 0° C. and again dialyzed against 700 mL stirred 1×PBS at 4° C. for 18 hours in a Microdialyzer unit (3,500 MWCO, Pierce). The resulting conjugate was analyzed by MALDI-TOF mass spectrometry and was found to be almost completely functionalized with a single biotin moiety.

Each of the following processes was conducted at room temperature with continuous rotation or mixing. The protein microarray surface was passivated by treatment with 1×TBS containing 0.05% Tween-20, and 1% BSA (200 μL) for 60 minutes. Biotinylated TNF-α (100 nM in 1×TBS, 0.02% Tween-20, and 0.2% BSA) was contacted with the microarray for 120 minutes at room temperature. The microarray was washed with 1×TBS containing 0.05% Tween-20 (3×50 mL, 5 minutes for each wash). Fluorescently labeled 2° agent (2.5 μg/mL Cy3-labeled anti-biotin monoclonal antibody (Sigma), made up in 1×TBS containing 0.05% Tween-20 and 0.2% BSA) was contacted with the microarray for 60 minutes. The microarray was washed with 1×TBS containing 0.05% Tween-20 (2×50 mL, 5 minutes each wash) followed by a 3 minute rinse with 1× TBS. Traces of liquid were removed by centrifugation, and the slide was allowed to air-dry at room temperature.

Figure 6A:
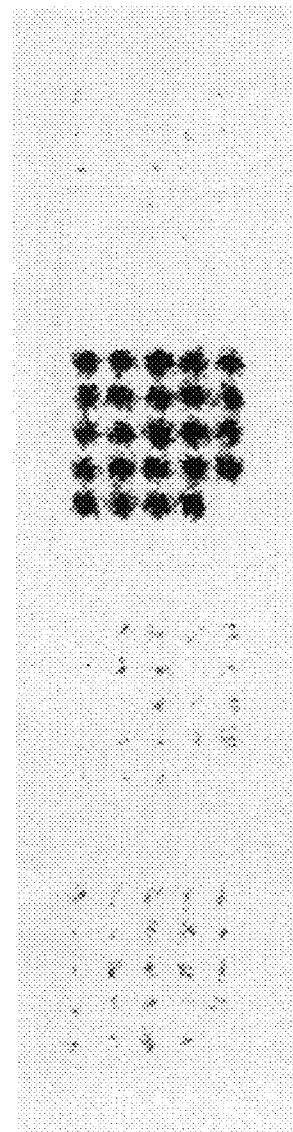
FIG. 6A is a phosphorimage of an exemplary microarray generated by the methods of the invention.
Figure 6B:
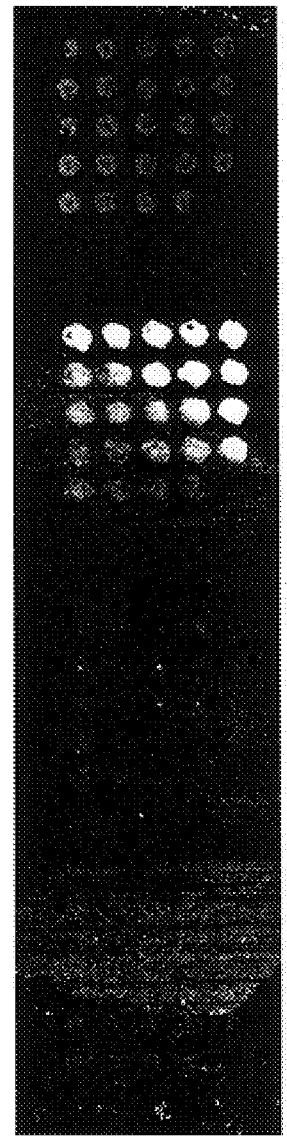
FIG. 6B is a fluorescence scan of an exemplary microarray generated by the methods of the invention.

Fluorescence laser scanning was performed with a GSI Lumonics ScanArray 5000 system using 10 μm pixel resolution and preset excitation and emission wavelengths for Cy3 dye. FIGS. 6A and 6B are the phosphorimage and fluorescence scan, respectively, of a microarray containing sorted FNTNF_LN-8. The phosphorimage demonstrates the location of the sorted polypeptide based on the $^{35}$S methionine signal. The fluorescence scan shows where the labeled TNF-α protein target has bound, demonstrating functionality of the sorted polypeptide.

The encoded IL-13 binder construct FNIL13_LN-16 was prepared as described above, and sorting was performed with the FNTIL13_LN-16 encoded DNA-protein fusions, as described above. The sorted polypeptide was visualized by direct detection of the $^{35}$S methionine on the fusion protein by phosphorimage analysis, as described above.

The functionality of the sorted polypeptide was demonstrated by binding to labeled IL-13 protein. Recombinant human IL-13 (500 μg, PeproTech) was biotinylated as described above. The resulting conjugate was analyzed by MALDI-TOF mass spectrometry and was found to be almost completely functionalized with a single biotin moiety. Binding of the biotinylated IL-13 protein followed by detection with Cy3-labeled anti-biotin monoclonal antibody was performed as described above.

Figure 7A:
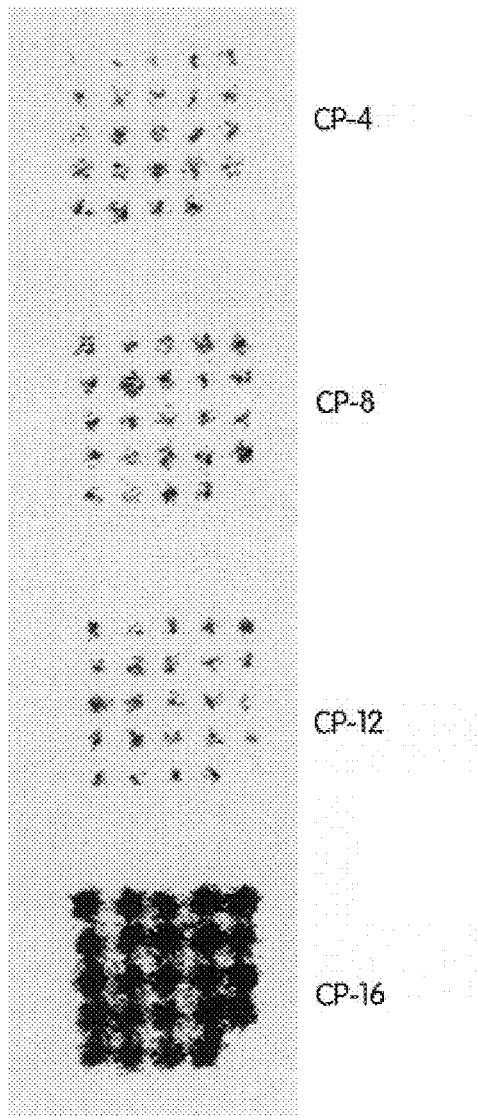
FIG. 7A is a phosphorimage of an exemplary microarray generated by the methods of the invention.
Figure 7B:
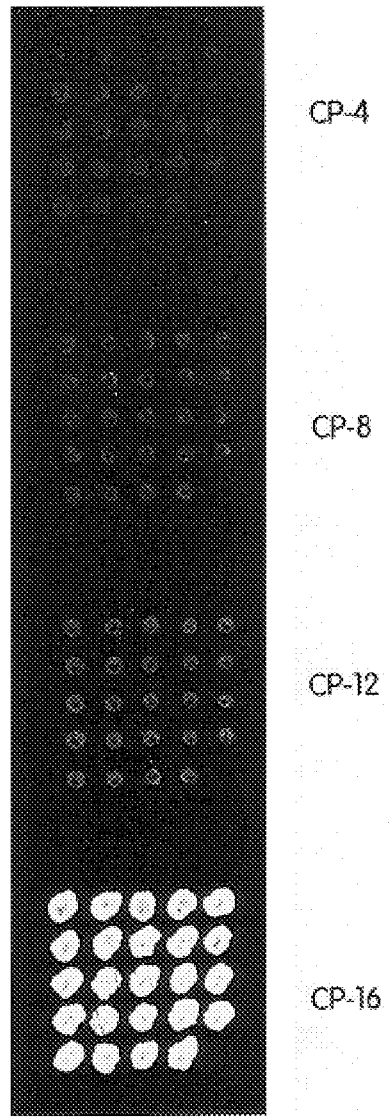
FIG. 7B is a fluorescence scan of an exemplary microarray generated by the methods of the invention.

FIGS. 7A and 7B are the phosphorimage and fluorescence scan, respectively, of a microarray containing sorted FNIL13_LN-16. The phosphorimage demonstrates the location of the sorted polypeptide based on the $^{35}$S methionine signal. The fluorescence scan shows where the labeled IL-13 protein target has bound, demonstrating functionality of the sorted polypeptide.

EXAMPLE 3

Figure 9A:
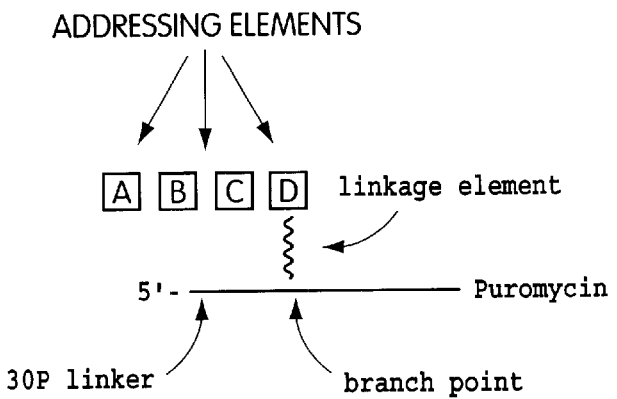
FIG. 9A is a schematic representation of an exemplary encoding molecule used to encode a protein as described in FIGS. 8A–8C, in general terms.
Figure 9B:
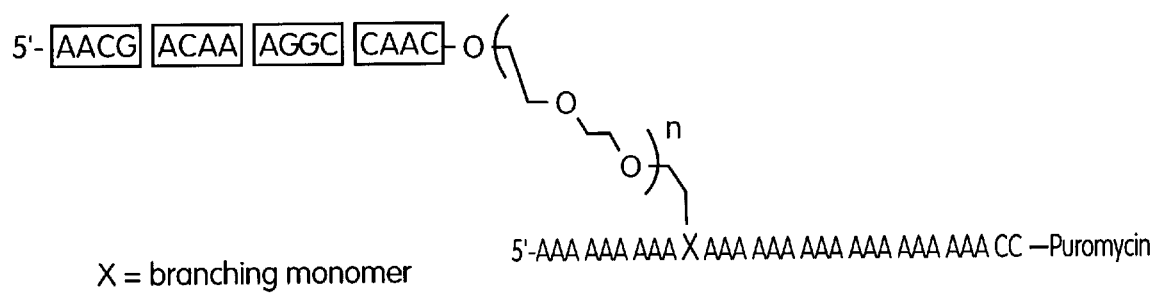
FIG. 9B is a schematic representation of an example of an encoding molecule (SEQ ID NO: 4) used in the invention, and as described in FIGS. 8A–8C, wherein X represents the branch point of the molecule, and the boxed nucleotide sequences (SEQ ID NO: 1) represent the addressing elements. The addressing element is attached to the DNA linker through a hexaethylene oxide linkage element.

Encoding and Sorting In Vitro Translated Proteins Using an Encoded Branched DNA Linker Yet another method for encoding in vitro translated proteins is shown in FIGS. 8A–8C. In this approach, an RNA encoding the desired protein to be in vitro translated is joined to a unique encoding molecule in the form of a branched encoded DNA linker. The DNA linker includes nucleic acids or nucleic acid analogs as shown in FIGS. 9A–9B. An addressing element, composed of nucleic acids or nucleic acid analogs, branches off from the DNA linker, to which it is attached by a linkage element.

Simple branched encoded DNA linker molecules can be assembled in the 3'→5' direction by conventional automated, solid-supported phosphoramidite oligonucleotide chemistry, for example, as described by Beaucage and Caruthers (supra). For example, the synthesis of the exemplary branched encoded DNA linker molecule shown in FIG. 9B begins with a solid support (e.g., controlled-pore glass or polystyrene) functionalized with a peptide acceptor, for example, puromycin at the nucleoside's 2'-hydroxyl group (Glen Research). Two C monomers are then added followed by 18 A monomers. A differentially protected asymmetric branching monomer (Clontech, Palo Alto, Calif.) is then added and the DMT protecting group is removed. Nine A monomers are subsequently added. The Lev protecting group on the branching monomer is then removed and four hexaethylene oxide monomer units (Glen Research) are added to provide the flexible linkage element. Next, the desired encoding sequence is built up by the stepwise addition of appropriate monomers. Design rules for specific encoding sequences are disclosed in U.S. Pat. No. 5,863,722. Once completed, branched encoded DNA linker molecules contain two 5'-termini. Upon completion of synthesis, the encoding molecule is cleaved from the support and deprotected in the usual fashion with ammonium hydroxide. Final purification is accomplished by standard chromatographic or electrophoretic techniques.

The simple branched encoded DNA linker molecules described above can be readily elaborated with affinity tags (e.g., biotin) and/or fluorophores (e.g., fluorescein) to give expanded branched encoded DNA linker molecules. Preferably, the affinity tag and fluorophore are each incorporated as nucleobase-functionalized T monomers (Glen Research) in the poly A region of the encoding molecule, replacing one/two of the 27 A monomers. The remainder of the encoding molecule is constructed as described above for the simple case.

The RNA and branched DNA linker are ligated using, for example, T4 DNA ligase. The ligated product is then in vitro translated according to the methods of Roberts and Szostak (supra) and Szostak et al. (supra), to form an RNA-protein fusion molecule, and the RNA portion of the molecule is then degraded as described in Example 1, and as shown in FIG. 8B. This RNA degradation step results in an in vitro translated protein attached to a branched encoded DNA linker.

The encoded in vitro translated protein may be hybridized to a universal chip or set of beads as shown in FIG. 8C. Hybridization occurs between the addressing element of the branched DNA linker and the capture probe of the solid support as described in Example 1.

Other embodiments are within the claims.

What is claimed is:

1. A method for encoding an in vitro translated protein, said method comprising the steps of:
   (a) providing an in vitro translated protein attached to a nucleic acid linker; and
   (b) binding an encoding molecule to said nucleic acid linker, thereby encoding said protein.

2. The method of claim 1, wherein said protein is derived from an RNA-protein fusion molecule.

3. The method of claim 1 or 2, wherein said encoding molecule comprises:
   (a) a unique addressing element;
   (b) a linker-specific alignment element; and
   (c) a linkage element positioned between said addressing element and said linker-specific alignment element.

4. The method of claim 1, wherein said encoding molecule is functionalized with a cross-linking moiety and said method further comprises cross-linking said encoding molecule to said protein.

5. The method of claim 3, wherein said encoding molecule comprises nucleic acids.

6. The method of claim 3, wherein said encoding molecule comprises nucleic acid analogs.

7. The method of claim 3, wherein said linkage element comprises polyethylene glycol units.

8. The method of claim 3, wherein said protein is bound to said encoding molecule through hybridization of said nucleic acid linker to said linker-specific alignment element.

9. The method of claim 7, wherein said polyethylene glycol units are hexaethylene oxide.

10. A method for encoding an in vitro translated protein, said method comprising the steps of:

(a) providing an in vitro translated protein; and (b) binding a nucleic acid linker to said protein, wherein said nucleic acid linker contains an addressing element, thereby encoding said protein.

11. The method of claim 10, wherein said protein is derived from an RNA-protein fusion molecule.

12. The method of claim 10, wherein said nucleic acid linker is functionalized with a cross-linking moiety and said method further comprises cross-linking said nucleic acid linker to said protein.

13. A method for encoding an in vitro translated protein, said method comprising the steps of:

(a) providing an in vitro translated protein; and (b) binding a nucleic acid linker to said protein, wherein an addressing element branches off from said nucleic acid linker, thereby encoding said protein.

14. The method of claim 13, wherein said protein is derived from an RNA-protein fusion molecule.

15. The method of claim 13, wherein said nucleic acid linker is functionalized with a cross-linking moiety and said method further comprises cross-linking said nucleic acid linker to said protein.

16. The method of claim 10, or 13, further comprising immobilizing said encoded protein formed in step (b) onto a solid support.

17. The method of claim 1, 10, or 13, wherein said protein is labeled with a reporter tag.

18. The method of claim 1, 10, or 13, wherein an affinity tag is attached to said encoding molecule and said method further comprises isolating said encoded protein using said affinity tag.

19. The method of claim 14, wherein said addressing element is bound to said nucleic acid linker by a linkage element.

20. The method of claim 19, wherein said linkage element comprises polyethylene glycol units.

21. The method of claim 20, wherein said polyethylene glycol units are hexaethylene oxide.

22. The method of claim 16, wherein said encoded protein is selected from a mixture of encoded proteins.

23. The method of claim 16, wherein said solid support is a glass or silica-based chip.

24. The method of claim 16, wherein said solid support is a bead.

25. The method of claim 16, wherein a capture probe is attached to said solid support.

26. The method of claim 16, wherein said solid support is functionalized with a cross-linking moiety and said method further comprises cross-linking said encoded protein to said solid support.

27. The method of claim 25, wherein said capture probe comprises nucleic acids.

28. The method of claim 25, wherein said capture probe comprises nucleic acid analogs.

29. The method of claim 25, wherein said encoded protein is immobilized onto said solid support by hybridization to said capture probe.

30. The method of claim 17, wherein said reporter tag is a fluorophore.

31. The method of claim 18, wherein said affinity tag is biotin.

32. The method of claim 4, 12, or 15, wherein said cross-linking moiety is chosen from the group consisting of psoralen, azido compounds, and sulfur-containing molecules.

33. The method of claim 4, wherein the 5' terminus of said encoding molecule is functionalized with an electrophile that cross-links regioselectively with a nucleophilic amino acid side chain of said protein.

34. The method of claim 26, wherein said cross-linking moiety is chosen from the group consisting of psoralen, azido compounds, and sulfur-containing molecules.

35. A method for detecting an interaction between a protein and a compound, said method comprising the steps of:

(a) providing an encoded in vitro translated protein immobilized onto a solid support;

(b) contacting said protein with a candidate compound under conditions which allow an interaction between said protein and said compound; and (c) analyzing said solid support for the presence of said compound as an indication of an interaction between said protein and said compound.

36. The method of claim 35, wherein said compound is a nucleic acid.

37. The method of claim 35, wherein said compound is a protein.

38. The method of claim 35, wherein said compound is a therapeutic.

39. The method of claim 35, wherein said compound is an enzyme.

40. An in vitro translated protein attached to a nucleic acid linker and bound to an encoding molecule.

41. An in vitro translated protein attached to an encoded nucleic acid linker molecule.

42. An in vitro translated protein attached to a branched encoded nucleic acid linker molecule.

43. The protein of claim 40, 41, or 42, attached to a solid support bearing a capture probe.

44. The protein of claim 40, 41, or 42, wherein said encoded protein is attached to said capture probe through hybridization.

45. The protein of claim 40, 41, or 42, wherein said encoded protein is attached to said capture probe through a covalent bond.

* * * * *

UNITED STATES PATENT AND TRADEMARK OFFICE
CERTIFICATE OF CORRECTION

PATENT NO. : 6,436,665 B1
DATED : August 20, 2002
INVENTOR(S) : Robert B. Kuimelis It is certified that error appears in the above-identified patent and that said Letters Patent is hereby corrected as shown below:

Title page,
Item [56], References Cited, OTHER PUBLICATIONS, in the Nielson *et al.* citation, replace "Science254" with -- Science 254 --;

Column 2,
Lines 6 and 42, replace "he" with -- the --.

Signed and Sealed this

Sixth Day of May, 2003

JAMES E. ROGAN
*Director of the United States Patent and Trademark Office*